US00PP08165P

United States Patent [19]

Hinshaw

[11] Patent Number: Plant 8,165

[45] Date of Patent: Mar. 2, 1993

[54] HINSHAW MUTANT WHITE PINE TREE

[75] Inventor: Joe S. Hinshaw, Lenoir, N.C.

[73] Assignee: Gailya T. Hinshaw, Lenoir, N.C.

[21] Appl. No.: 720,733

[22] Filed: Jun. 25, 1991

[51] Int. Cl.[5] ..... A01H 5/00

[52] U.S. Cl. ..... Plt./50.1

[58] Field of Search ..... Plt./50.1

*Primary Examiner*—James R. Feyrer

*Attorney, Agent, or Firm*—Shefte, Pinckney & Sawyer

[57] ABSTRACT

A conspicuously striking pine tree member of *Pinus strobus* with the unique ability to form clonal specimens of narrow conic to columnar figure; having dense, fine branching which is not layered in appearance and attractive foliage coloration; and forming tall, narrow specimens which can be planted at unusually high density for effect and landscaping or for high production of timber.

2 Drawing Sheets

BRIEF SUMMARY OF THE INVENTION

The present invention relates to pine trees of the species *Pinus strobus* and particularly to a new and distinct variety of white pine tree which has been denominated 'Hinshaw Mutant'. The 'Hinshaw Mutant' white pine tree of the present invention features branches which grow in annular whorls forming a tree which grows sharply upwardly forming a canopy having a very acute angle relative to the trunk. This tree provides a tall narrow pine tree of dense foliage which is suitable for landscaping, and for dense plantings for high production of timber.

The present invention relates to a new and distinct variety of white pine tree of the genus and species *Pinus strobus*. The pine tree of the present invention was newly found, being discovered in Graham County, a mountainous county in the far western portion of North Carolina at the lower edge of a pasture-type field with an elevation of approximately 2,000 feet.

The primary characteristics of this new variety which connote its distinctive advance over existing types are the branches which grow in annual whorls, growing sharply upwardly forming a very acute angle with the trunk. This branch growth creates a very narrow, compact crown in relation to the tree height. The vigor of the pine tree of the present invention is evidenced by 12 inches to 30 inches of terminal growth per year, depending on the quality of the growing season, of a 14 year-old specimen which was grown in an open pasture area with southeastern exposure in Caldwell County in west central North Carolina. The maximum crown spread is typically eight feed on a specimen twenty-five feet tall. There are, on average, ten to twelve branches per whorl. The size of the branches are typically equal to the branch size for the genus and species *Pinus strobus*. The tree is capable of such growth whether shaded or in open sunlight. In addition, the old bark is slow to develop furrows. This tree is useful for landscaping and for high density planting for wood production. The pine tree of the present was discovered and asexually propagated by myself or by my direction, by grafting. Clones of the tree have been found to be substantially identical to the parent tree in every distinguishing characteristic.

This tree is particularly distinguished from other members of the species by its growth habit which forms a tree of narrow conical or columnar figure due to the narrow crotch angles of the branches. The detailed botanical characteristics of the tree are otherwise quite similar to those of the species.

The branches of the tree according to the present invention are no more susceptible than the parent species to sloughing or self-pruning. Lateral branches are no more susceptible to shearing due to the forces of weather as compared to the species in general. The branches do not reflex away from the trunk with increased elongation and weight due to the advancing growth and age. The expected height of a mature specimen is approximately fifty feet with a narrow conical shape and a spread of eight to fourteen feet. The coloration of the various parts of the tree according to the present invention does not substantially differ from those of the species. The leaf sheaths are comparable to those of *Pinus strobus*. The present invention readily sets seeds or samara in cones typical of the species, and readily cross pollinates with other trees of the species. Seeds from the mutant tree readily germinate and produce vigorous standard *Pinus strobus* seedlings which cross-back readily with other specimens within *Pinus strobus*.

The resin producing ability of the tree is comparable too *Pinus strobus*. A clone might first produce cones or seeds at two years from graft placement depending on the stock. The samara and cones of the present invention are comparable to those of *Pinus strobus*. The bark of the tree of the present invention is comparable to the bark of *Pinus strobus*. However, the bark is typically not as furrowed as that of the root stock, which is generally true of any graft. The tree of the present invention exhibits good union between the root stock and the graft stock with no rejection tendencies and no swelling.

BRIEF DESCRIPTION OF THE VIEWS OF THE DRAWING

Sheet 1 is an elevation view photograph 'Hinshaw Mutant' white pine tree.

Sheet 2 is a close-up view photograph of 'Hinshaw Mutant' white pine tree as seen in Sheet 1, showing in greater detail the needles, cones, branches and bark of the tree of the invention.

DETAILED BOTANICAL DESCRIPTION

The following is a detailed botanical description of the new variety:

Type: Eastern white pine tree, for landscaping and wood production.

Family: Pinaceae.

*Genus.*—Pinus.

*Species.*—strobus.

Commercial: White pine, variety 'Hinshaw Mutant'.

Propagation: Holds its distinguishing characteristics through succeeding propagations by asexual reproduction; specifically, by grafting.

Locality where grown: Lenoir, N.C.

Growth habit: Branches are formed with exceedlingly narrow, acute angles relative to the trunk, resulting in a tree of narrow conic figure. Branches are strongly ascending and maintain their position with increasing age. Canopy is much narrower and denser than that of a tree typical of the species.

Vigor: Vigor of this tree is substantially the same as the species, and is exemplified by growth of about 12–30 inches of terminal growth per year for a specimen of about 14 years old. Vigor is affected by quality of the growing season as is characteristic within the species.

Needles: Three and one half to five inches long, in fascicles of 5, slender and flexible, ventrally has three to five rows of stomates forming white lines; persist for two growing seasons. Foliage coloration and characteristics and sheath characteristics are generally like those of the species.

Cones: Four to eight inches long, narrow oblong-conic and curved, stacked with thin scales; maturing and generally shedding after second growing season or during the following winter; scales nearly smooth and unarmed. Generally, typical of the species.

Twigs: Orange-brown, glabrous or sparingly puberulent.

Buds: Covered with thin reddish or orange-brown scales. Typical of the species.

Bark: Thin and smooth, dark green. Old bark slow to develop furrow, particularly when compared with that of the typical seedling rootstock.

Branches: Whorled, strongly ascending, forming an angle of about five to twenty-five degrees with the trunk; forming compact growth against the trunk, thus creating a very attenuate crown.

I claim:

1. A new and distinct variety of white pine tree substantially as described and illustrated, characterized as to novelty by its strongly ascending, whorled branches, forming acute angles with the trunk.

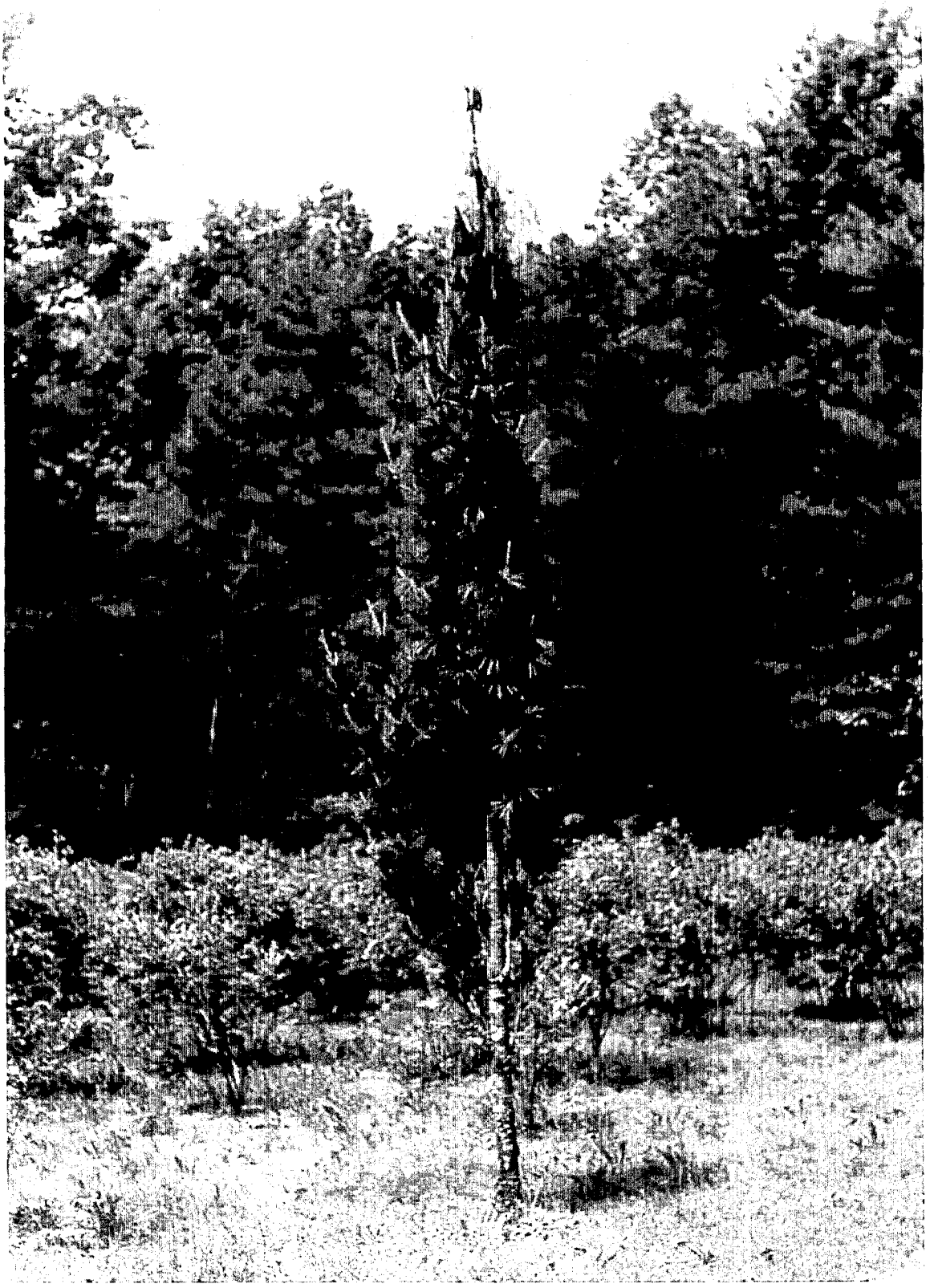

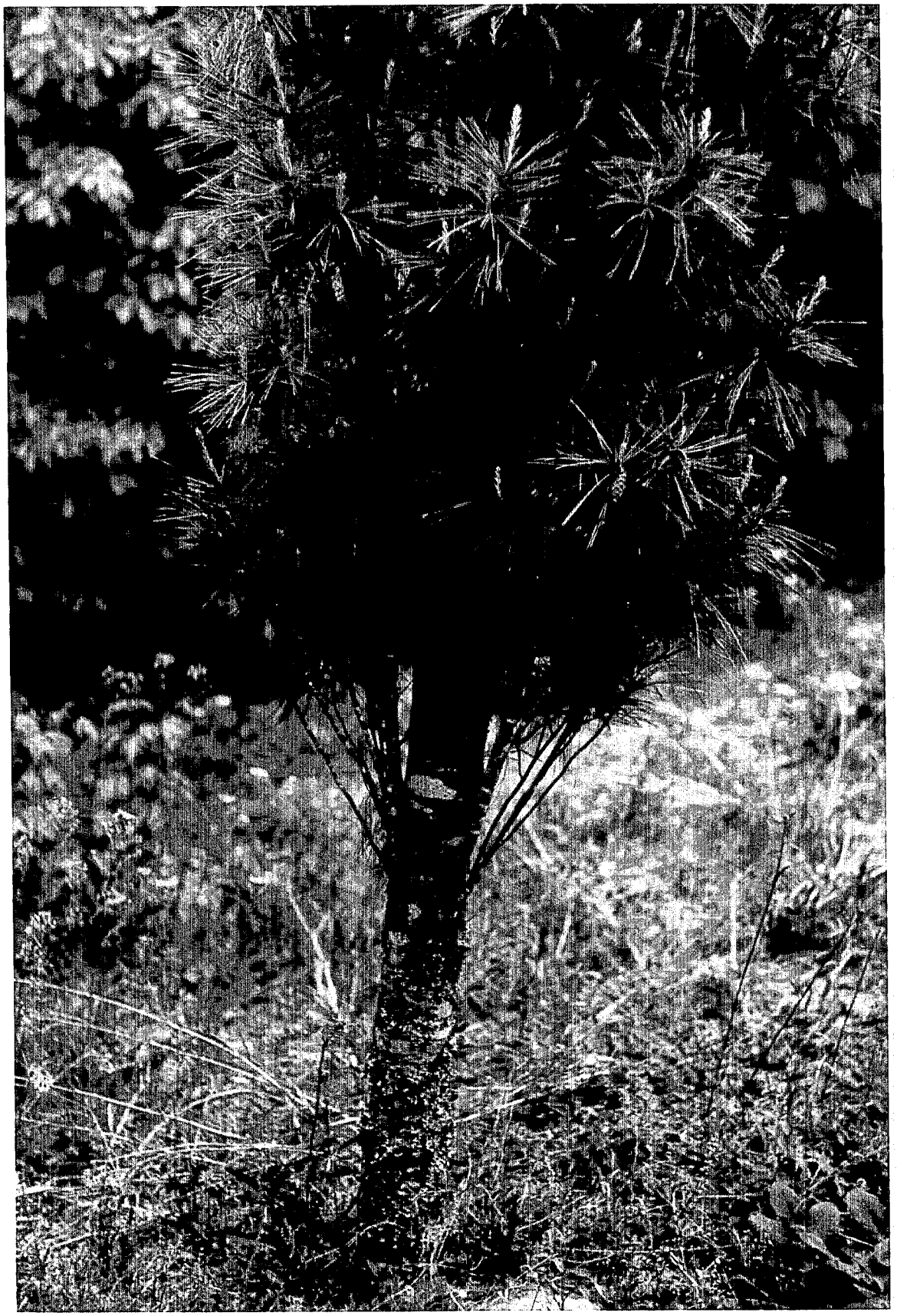

* * * * *